United States Patent [19]

Musser et al.

[11] Patent Number: 4,876,346
[45] Date of Patent: Oct. 24, 1989

[54] QUINOLINE COMPOUNDS

[75] Inventors: John H. Musser, Malvern; Anthony F. Kreft, III, Trooper; Reinhold H. W. Bender, Valley Forge, all of Pa.

[73] Assignee: American Home Products Corporation, New York, N.Y.

[21] Appl. No.: 863,666

[22] Filed: May 15, 1986

Related U.S. Application Data

[63] Continuation-in-part of Ser. No. 729,509, May 2, 1985, abandoned.

[51] Int. Cl.⁴ ................... C07D 215/14; C07D 215/16
[52] U.S. Cl. ..................... 546/172; 546/157; 546/174; 546/175; 546/176
[58] Field of Search ............... 546/174, 157, 172, 176, 546/175; 514/311, 312

[56]  References Cited

U.S. PATENT DOCUMENTS

| | | | |
|---|---|---|---|
| 4,532,349 | 7/1985 | Lang et al. | 564/194 |
| 4,661,499 | 4/1987 | Young et al. | 514/311 |
| 4,761,419 | 8/1988 | Picard et al. | 546/174 |
| 4,788,204 | 11/1988 | Benevides et al. | 514/311 |

Primary Examiner—David B. Springer
Attorney, Agent, or Firm—George Tarnowski

[57]  ABSTRACT

There are disclosed compounds of the formula

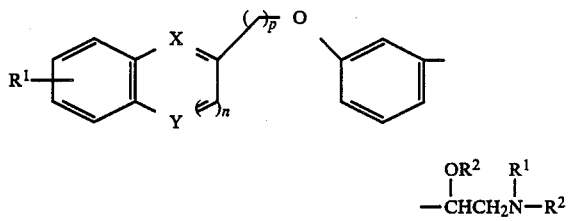

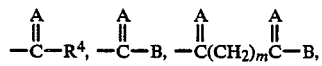

wherein
X is N or $CR^1$
Y is O, S, $NR^1$, $CHR^1$ or $C(R^1)_2$ when n=0, or N or $CR^1$ when n=1;
p is 0–3;
$R^1$ is hydrogen or lower alkyl;
$R^2$ is H, $$-\overset{A}{\underset{\|}{C}}-R^4, \quad -\overset{A}{\underset{\|}{C}}-B, \quad -\overset{A}{\underset{\|}{C}}(CH_2)_m\overset{A}{\underset{\|}{C}}-B,$$

$-SO_2R^3$ or $-SO_2N(R^3)_2$, lower alkyl, lower alkenyl, lower alkynyl or lower alkyl carbonyl prolinate;
$R^3$ is H, lower alkyl or perfluoro lower alkyl;
$R^4$ is lower alkyl, phenyl, pyridyl or thienyl;
$R^5$ is hydrogen, lower alkyl, phenyl or pyridyl;
A is O or $NR^1$;
B is $OR^1$ or $N(R^5)_2$;
m is 0–2;

and the pharmaceutically acceptable salts thereof, and their use in the treatment of leukotriene-mediated nasobronchial obstructive airpassageway conditions, such as allergic rhinitis, allergic bronchial asthma and the like.

20 Claims, No Drawings

QUINOLINE COMPOUNDS

This application is a continuation-in-part of U.S. Ser. No. 729,509, filed May 2, 1985, abandoned.

This invention relates to novel heterocyclic compounds possessing lipoxygenase inhibitory and slow-reacting substance of anaphylaxis (SRS-A) antagonist activity, which are useful as anti-inflammatory and anti-allergic agents.

It is known that arachidonic acid (AA) is metabolized in mammals by two distinct pathways. The metabolism of arachidonic acid by cyclooxygenase enzymes results in the production of prostaglandins and thromboxanes. The physiological activity of the prostaglandins has already been amply elucidated in recent years. The other pathway of AA metabolism involves lipoxygenase enzymes and results in the production of a number of oxidative products called leukotrienes. The latter are designated by the LT nomenclature system, and the most significant products of the lipoxygenase metabolic pathway are the leukotrienes $C_4$ and $D_4$. The substance denominated slow-reacting substance of anaphylaxis (SRS-A) has been shown to consist of a mixture of leukotrienes, with $LTC_4$ and $LTD_4$ as the primary products and having varying amounts of other leukotriene metabolites [see Bach et al., *J. Immun.* 215, 115–118 (1980); *Biochem. Biophys. Res. Commun.* 93, 1121–1126 (1980)].

The significance of these leukotrienes is that a great deal of evidence is accumulating showing that leukotrienes participate in inflammatory reactions, exhibit chemotactic activities, stimulate lysosomal enzyme release and act as important factors in the immediate hypersensitivity reaction. It has been shown that $LTC_4$ and $LTD_4$ are potent bronchoconstrictors of the human bronchi [see Dahlen et al., *Nature* 288, 484–486 (1980)], and another leukotriene, $LTB_4$, is a powerful chemotactic factor for leukocytes [see A. W. Ford-Hutchinson, *J. Roy. Soc. Med.*, 74, 831–833 (1981)]. The activity of leukotrienes and slow-reacting substances (SRS's) as mediators of inflammation and hypersensitivity is extensively reviewed in Bailey and Casey, *Ann. Reports Med. Chem.*, 17, 203–217 (1982).

The biological activity of the leukotrienes and SRS's, and of lipoxygenase as the enzyme leading to the metabolism of AA to leukotrienes, indicates that a rational approach to drug therapy to prevent, remove or ameliorate the symptoms of allergies, anaphylaxis, asthma and inflammation must focus on either blocking the release of mediators of these conditions or to antagonize their effects. Thus, compounds which inhibit the biological effects of the leukotrienes and SRS's and/or which control the biosynthesis of these substances, as by inhibiting lipoxygenase, are considered to be of value in treating such conditions as allergic bronchial asthma, allergic rhinits, as well as in other immediate hypersensitivity reactions.

The invention provides novel compounds of the formula

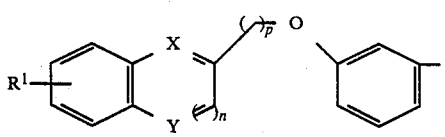

-continued

wherein
X is N or $CR^1$
Y is O, S, $NR^1$, $CHR^1$ or $C(R^1)_2$ when n=0, or N or $CR^1$ when n=1;
p is 0–3;
$R^1$ is hydrogen or lower alkyl;
$R^2$ is H,

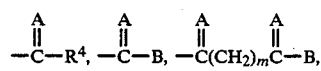

—$SO_2R^3$ or —$SO_2N(R^3)_2$, lower alkyl, lower alkenyl, lower alkynyl or lower alkyl carbonyl prolinate;
$R^3$ is H, lower alkyl or perfluoro lower alkyl;
$R^4$ is lower alkyl, phenyl, pyridyl or thienyl;
$R^5$ is hydrogen, lower alkyl, phenyl or pyridyl;
A is O or $NR^1$;
B is $OR^1$ or $N(R^5)_2$;
m is 0–2;
and the pharmaceutically acceptable salts thereof.

The term "lower alkyl" refers to moities having 1 to 6 carbon atoms in the carbon chain.

The compounds of the invention can be prepared by the reaction of an appropriate R—, S— or racemic phenylephrine; R—, S— or racemic norphenylephrine; R—, S— or racemic N-ethylphenylephrine; or R—, S— or racemic N-ethylnorphenylephrine derivative with an appropriate benzo-fused heterocyclic derivative as follows:

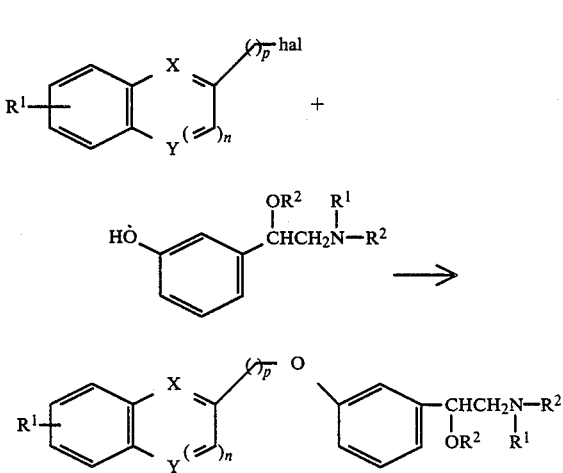

wherein X, Y, $R^1$, $R^2$, n and p are as defined hereinbefore and hal refers to a halo radical, for example, chloro or bromo. The reaction is carried out in the presence of cesium carbonate in an organic solvent, for instance acetone, under reflux conditions.

The various starting phenylephrine-based derivatives employed in the reaction sequence can be prepared as follows (illustrating preparation of a phenylephrine starting material):

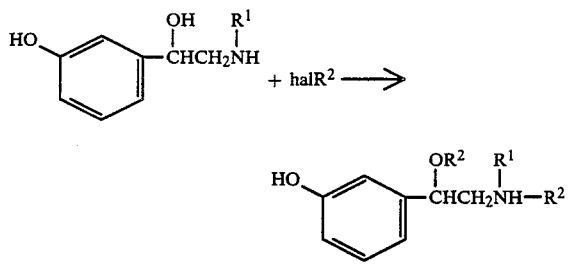

The starting enzo-fused heterocyclic compounds used in the reaction sequence are either commercially available or can be prepared by conventional preparative methods readily apparent to those skilled in the art.

Compounds of the invention which contain a basic nitrogen are capable of forming pharmacologically acceptable salts, including the salts of pharmacologically acceptable organic and inorganic acids such as hydrochloric, hydrobromic, sulfuric, nitric, phosphoric, methanesulfonic, benzenesulfonic, acetic, citric, fumaric, maleic, succinic and the like.

The compounds of the invention, by virtue of their ability to inhibit the activity of lipoxygenase enzyme and by their ability to antagonize the effects of $LTD_4$ and $LTC_4$, which are the major constituents of SRS-A, are useful for the inhibition of symptoms induced by these leukotrienes. Accordingly, the compounds are indicated in the prevention and treatment of those disease states in which $LTD_4$ and $LTC_4$ are causative factors, for example allergic rhinitis, allergic bronchial asthma and other leukotriene mediated naso-bronchial obstructive air-passageway conditions, as well as in other immediate hypersensitivity reactions, such as allergic conjunctivitis. The compounds are especially valuable in the prevention and treatment of allergic bronchial asthma.

When the compounds of the invention are employed in the treatment of allergic airways disorders, they can be formulated into oral dosage forms such as tablets, capsules and the like. The compounds can be administered alone or by combining them with conventional carriers, such as magnesium carbonate, magnesium stearate, talc, sugar, lactose, pectin, dextrin, starch, gelatin, tragacanth, methylcellulose, sodium carboxymethylcellulose, low melting wax, cocoa butter and the like. Diluents, flavoring agents, solubilizers, lubricants, suspending agents, binders, tablet-disintegrating agents and the like may be employed. The compounds may be encapsulated with or without other carriers. In all cases, the proportion of active ingredients in said compositions both solid and liquid will be at least to impart the desired activity thereto an oral administration. The compounds may also be injected parenterally, in which case they are used in the form of a sterile solution containing other solutes, for example, enough saline or glucose to make the solution isotonic. For administration by inhalation or insufflation, the compounds may be formulated into an aqueous or partially aqueous solution, which can then be utilized in the form of an aerosol.

The dosage requirements vary with the particular compositions employed, the route of administration, the severity of the symptoms presented and the particular subject being treated. Treatment will generally be initiated with small dosage less than the optimum dose of the compound. Thereafter the dosage is increased until the optimum effect under the circumstances is reached.

In general, the compounds of the invention are most desirably administered at a concentration that will generally afford effective results without causing any harmful or deleterious side effects, and can be administered either as a single unit dose, or if desired, the dosage may be divided into convenient subunits administered at suitable times throughout the day.

The lipoxygenase inhibitory and leukotriene antagonist effects of the compounds of the invention may be demonstrated by standard pharmacological procedures, which are described more fully in the examples given hereinafter.

These procedures illustrate the ability of the compounds to inhibit the polymorphonuclear leukocyte synthesis of the lipoxygenase product 5-HETE, the ability of the compounds to antagonize $LTD_4$-induced bronchospasm mediated by exogenously administered leukotrienes and measure the in vivo activity of the compounds as lipoxygenase inhibitors and leukotriene antagonists of endogeneous mediators of bronchospasm.

The following examples show the preparation and pharmacological testing of compounds within the invention.

EXAMPLE 1

(1R)-1-[3-[(2-Benzthiazoyl)-methoxy]phenyl]-2-(N-methyl-N-diethylcarbamoyl)amino ethanol (A)

(1R)-1-(3-Hydroxyphenyl)-2-(N-methyl-N-diethylcarbamoyl)amino ethanol

To a suspension of 1R-phenylephrine hydrochloride (40.6 g, 0.2 mol) in tetrahydrofuran (1 L) and triethylamine (56 ml, 0.4 mol) is added diethyl carbamoyl chloride (27.1 g, 0.2 mol) in tetrahydrofuran. The reaction is stirred for 1 hour and filtered through Celite and silica gel. The solvent is removed in vacuo giving 38.1 g (76% yield) of product as an oil.

(B) 2-Chloromethylbenzthiazole

To a solution of aminothiophenol (8.3 g) in methylene chloride at 0° C. is added methyl chloroacetamidate hydrochloride [prepared according to procedures described by R. Rogers and D. G. Nelson, Chem. Rev., 61, 179 (1961)] (8.6 g). The reaction is allowed to warm to room temperature while stirring overnight. The mixture is washed with water (3X), dried over magnesium sulfate, and concentrated to an oil. The oil is distilled (120°–135° C. at 0.5 mm Hg) to give 7.8 g (71% yield) of product.

(C)

(1R)-1-[3-[(2-Benzthiazolyl)-methoxy]phenyl]-2-(N-methyl-N-diethylcarbamoyl)amino ethanol A mixture of (1R)-1-(3-hydroxyphenyl)-2-(N-methyl-N-diethylcarbamoyl)amino ethanol (5.0 g, 0.02 mol), 2-chloromethylbenzthiazole (3.4 g, 0.02 mol), cesium carbonate (6.0 g) and acetone (500 ml) is refluxed for 2 days. The mixture is filtered through Celite and silica gel and the solvent is removed in vacuo. The remaining oil is purified by HPLC using ethyl acetate/methylene chloride (25:75) as an eluent. The desired product is isolated and crystallized from ethyl ether to give 1.6 g (20% yield) of solid, m.p. 60°–63° C.

EXAMPLE 2

Following the procedures of Example 1 and using appropriate starting materials and reagents, the following compounds are prepared:

(A) (1R)-1-[3-[(1-Methyl-2-benzimidazoyl)methoxy]phenyl]-2-(N-methyl-N-diethylcarbamoyl)amino ethanol, melting point 138°–141° C.

(B) (1R)-1-[3-[(2-Quinolinyl)methoxy]phenyl]-2-(N-methyl-N-diethylcarbamoyl)amino ethanol, melting point 71°–74° C.; $[\alpha]_D^{26} = +20.99$ in $CHCl_3$.

(C) (1R)-1-[3-[(1-Methyl-2-benzimidazoyl)methoxy]phenyl]-2-(N-methyl-N-propanoyl)amino ethanol, melting point 143°–144° C.

(D) (1R)-1-[3-[(2-Quinolinyl)methoxy]phenyl]-2-[N-methyl-N-(4-pyridinoyl)]amino ethanol, melting point 141°–144° C.

(E) (1R)-1-[3-[(2-Quinolinyl)methoxy]phenyl]-2-(N-methyl-N-diphenylcarbamoyl)amino ethanol, hydrochloride, melting point 153°–156° C.

(F) (1R)-1-[3-[(2-Quinolinyl)methoxy]phenyl]-2-(N-methyl-N-dimethylcarbamoyl)amino ethanol, melting point 109°–110° C.

(G) (1R)-1-[3-[(2-Quinolinyl)methoxy]phenyl]-2-(N-ethyl-N-diethylcarbamoyl)amino ethanol, oil.

(H) (1R)-1-[3-[(2-Quinolinyl)methoxy]phenyl]-2-(N-methyl-N-dimethylsulfamoyl)amino ethanol, melting point 89°–91° C.

(I) (S)-1-[[[(R)-2-Hydroxy-2-[3-(2-quinolinylmethoxy)phenyl]ethyl]methylamino]carbonyl]-2-pyrrolidine carboxylic acid, methyl ester, hydrochloride, melting point 75° C. dec.

(J) (1S)-1-[3-[(2-Quinolinyl)methoxy]phenyl]-2-(N-methyl-N-diethylcarbamoyl)amino ethanol, melting point 69°–72° C.; $[\alpha]_D^{26} = -20.18$ in $CHCl_3$ (compare with Example 2B).

(K) (1R)-1-[3-[(2-Quinolinyl)methoxy]phenyl]-2-(N-methyl-N-ethylcarboxylate)amino ethanol, melting point 69°–71° C.

(L) 1-[3-[(2-Quinolinyl)methoxy]phenyl]-2-(N-ethylcarboxylate)amino ethanol, melting point 98°–100° C.

EXAMPLE 3

(1R)-1-[3-[(2-Quinolinyl)methoxy]phenoxy]-2-(N-ethylcarbamoyl)amino ethanol (A)

(1R)-1-(3-Hydroxyphenyl)-2-(N-ethylcarbamoyl)amino ethanol

To a suspension of R-phenylephrine (10.0 g, 59.8 mmol) in diethyl ether (200 ml) with triethylamine (4 drops) is added ethyl isocyanate (4.25 g, 59.8 mmol) in diethyl ether (50 ml). The reaction is allowed to stir overnight at room temperature. A white suspension forms which is decanted from the precipitated gum, filtered and dried giving 3.0 g (21% yield) of product, m.p. 102°–105° C.

(B)

(1R)-1-[3-[(2-Quinolinyl)methoxy]phenyl]-2-(N-ethylcarbamoyl)amino ethanol

This compound is prepared in the same manner as Example 1C using 2-chloromethylquinoline (2.6 g, 12.6 mmol) and the compound of 3A (3.0 g, 12.6 mmol) above. The title compound is purified by preparative HPLC giving 3.7 g (77% yield) of an oil.

EXAMPLE 4

(1R)-1-[3-[(2-Quinolinyl)methoxy]phenyl]-2-(N-methylcarbamoyl)amino ethanol

The title compound is prepared in the same manner as Example 3 except methyl isocyanate (1.5 g, 6.69 mmol) is employed in place of ethyl isocyanate. The title compound is obtained in 69% yield as an oil.

EXAMPLE 5

Ethylcarbamic acid (1R)-2-[[(ethylamino)carbonyl]methylamino]-1-[3-(2-quinolinylmethoxy)phenyl]ethyl ester, hydrochloride (A) Ethylcarbamic acid (1R)-2-[[(ethylamino)carbonyl]methylamine]ethyl ester This compound is prepared in the same manner as Example 3A except 2-equivalents of ethyl isocyanate are employed.

(B) Ethylcarbamic acid (1R)-2-[[(ethylamino)carbamoyl]methylamino]-1-[3-(2-quinolinylmethoxy)phenyl]ethyl ester, hydrochloride The title compound is prepared in the same manner as in Example 3B using the compound of 5A above, m.p. 86°–88° C.

EXAMPLE 6

N-[2-Hydroxy-2-[3-(2-quinolinylmethoxy)phenyl]ethyl]-2-pyridine carboxamide (A)
4,5-Dihydro-5-(3-hydroxyphenyl)-2-(2-pyridyl)-1,3-oxazole A mixture of (±) norphenylephrine hydrochloride (10 g, 0.05 mol) and methyl iminopicolinate (8 g, 0.059 mol) in tetrahydrofuran (300 ml) is heated to reflux for 16 hours. The mixture is dissolved in ethyl acetate and water. The aqueous layer is extracted twice with ethyl acetate. The combined ethyl acetate solutions are washed twice with dilute aqueous sodium chloride solution, dried over anhydrous magnesium sulfate and concentrated to dryness to obtain a partially crystalline material. This material is triturated with ethyl ether to obtain crystals. These crystals are dissolved in hot acetonitrile and the hot solution is filtered and allowed to cool. The crystals (4 g) are filtered off, washed with acetonitrile and dried in vacuo, m.p. 139°–141° C.

(B)
4,5-Dihydro-5-[3-[(2-quinolinyl)methoxy]phenyl]-2-(2-pyridyl)-1,3-oxazole

A solution of 4,5-dihydro-5-(3-hydroxyphenyl)-2-(2-pyridyl)-1,3-oxazole (7.3 g, 0.03 mol) and 2-(chloromethyl)quinoline (5.4 g, 0.03 mol) in dimethylformamide (200 ml) is heated to 90° for 16 hours in the presence of sodium methoxide (1.6, 0.03 mol). The mixture is dissolved in ethyl acetate and water. The aqueous layer is extracted twice with ethyl acetate. The combined ethyl acetate solutions are washed twice with dilute aqueous sodium chloride solution, dried over anhydrous magnesium sulfate and concentrated to obtain an oil. This material is chromatographed on a Water Prep Pak 500 silica column with methylene chloride/methanol 99/1 (v/v) as mobile phase to obtain 2.5 g of purified material as a viscous oil.

(C)
N-[2-Hydroxy-2-[3(2-quinolinylmethoxy)phenyl]ethyl]-2-pyridine carboxamide

A solution of 3.9 g (0.01 mol) of 4,5-dihydro-5-[3-[(2-quinolinyl)methoxy]phenyl]-2-(2-pyridyl)-1,3-oxazole in 100 ml of acetonitrile, 10 ml of water, and 1 ml of concentrated hydrochloric acid is heated on a steam bath for 5 hours. The solvents are evaporated and the residue is dissolved in a mixture of aqueous sodium bicarbonate and ethyl acetate. The ethyl acetate solution is separated and washed with dilute aqueous sodium chloride solution. The ethyl acetate solution is dried over anhydrous magnesium sulfate, filtered, and evaporated. The residue is dissolved in hot ethyl acetate and the solution is distilled with hexane to obtain crystals (2.2 g), m.p. 126°–129° C.

EXAMPLE 7

Following the procedures of Example 6 and using appropriate starting materials and reagents, the following compounds are prepared:

(A) N-[2-Hydroxy-2-[3-(2-quinolinyl)phenyl]ethyl]benzamide, m.p. 118°–120° C.
(B) N-[2-Hydroxy-2-[3-(2-quinolinylmethoxy)phenyl]ethyl]-2-thiophene carboxamide, m.p. 140°–142° C.
(C) 3-[[2-Hydroxy-2-[3-(2-quinolinylmethoxy)phenyl]ethyl]amino]-3-oxopropanoic acid, ethyl ester.

EXAMPLE 8

α-[[Methyl-(2-propynyl)amino]methyl]-3-(2-quinolinylmethoxy)benzene methanol (A)
(R)-3-Hydroxy-α-[[methyl-(2-propynyl)amino]methyl]-benzene methanol To a mixture of 20 g (0.098 mol) of R(−)phenylephrine hydrochloride, 20 g (0.2 mol) triethylamine and 300 ml of tetrahydrofuran is added a mixture of 12 g (0.1 mol) of propargyl bromide and 3 g of toluene over a period of ½ hour. The mixture is stirred for 16 hours and poured into water and ethyl acetate. The ethyl acetate is separated and the aqueous phase is extracted twice with ethyl acetate. The combined ethyl acetate is washed twice with dilute aqueous sodium chloride solution, dried over anhydrous magnesium sulfate, filtered and concentrated to obtain crystals (14 g) m.p. 102°–103° C. The crystals are dissolved in hot ethyl acetate and the solution is diluted with hexane to obtain crystals (8.8 g) m.p. 102°–103° C.

(B)
α-[[Methyl-(2-propynyl)amino]methyl]-3-(2-quinolinylmethoxy)benzene methanol A mixture of 8.2 g (0.04 mol) of (R)-3-hydroxy-α-[[methyl-(2-propynyl)amino]methyl]benzene methanol, 7.1 g (0.04 mol) of 2-(chloromethyl)quinoline, 13.5 g (0.04 mol) of cesium carbonate, 0.5 g of potassium iodide, and 500 ml of tetrahydrofuran is heated for 10 hours with stirring. The mixture is poured into water and ethyl acetate. The ethyl acetate is separated and washed with dilute aqueous sodium chloride solution. The ethyl acetate is dried over anhydrous magnesium sulfate, filtered and evaporated. The residue is chromatographed on silica gel with methylene chloride/isopropanol as eluent. Fractions 11–17 are combined, the solvent is evaporated and the residue, a viscous oil (2.1 g) is dried in vacuo.

EXAMPLE 9

1,1,1-Trifluoro-N-[2-hydroxy-2-[3-(2-quinolinylmethoxy)phenyl]ethyl]methane sulfonamide (A)
5-[3-(2-Quinolinylmethoxy)phenyl]-2-oxazolidinone A mixture of 1-[(2-quinolinyl)methoxy]phenyl]-2-(N-ethylcarboxylate)amino ethanol (49.0 g, 0.134 mol) of Example 2L, acetone (400 ml) and cesium carbonate (4.5 g) is refluxed for 5 days. The reaction mixture is filtered and the solvent removed in vacuo. The remaining oil is purified by HPLC using ethyl acetate and hexane as an eluent. The title compound is isolated and crystallized from acetone giving 14.5 g (34% yield) of solid, m.p. 137°–140° C.

(B)
1,1,1-Trifluoro-N-[2-hydroxy-2-[3-(2-quinolinylmethoxy)phenyl]ethyl]methane sulfonamide To a solution of 6.4 g (0.02 mol) of 5-[3-(2-quinolinylmethoxy)phenyl]-2-oxazolidinone, 2.6 g (0.02 mol) of diisopropylethylamine in 200 ml of methylene chloride is added a solution of 6.5 g (0.023 mol) of trifluoromethane sulfonic acid anhydride in 100 ml of methylene chloride over ½ hour while cooling to −70° C. The mixture is allowed to warm to room temperature over a period of 2 hours and the solvent is evaporated. The residue is dissolved in 100 ml of methanol and 60 ml of Claisen's alkali and the mixture is stirred for 1 hour at 28° C. The mixture is diluted with water, washed with methylene chloride and acidified to pH 3. The solution is extracted twice with methylene chloride. The methylene chloride is dried over anhydrous magnesium sulfate, filtered and evaporated to obtain a greenish residue (5.6 g). The greenish residue is triturated with diethyl ether to obtain crystals (2.4 g). The crystals are chromatographed on silica gel with hexane and ethyl acetate as eluent. Fractions 4–6 are combined, the solvent is evaporated and the residue is triturated with ethyl ether to obtain crystals (1.5 mg) m.p. 142°–144° C.

EXAMPLE 10

The compounds 5- and 12-hydroxyeicosatetraenoic acid (5-HETE and 12-HETE and 5,12-dihydroxyeicosatetraenoic acid (5,12-diHETE) are early arachidonic acid oxidation products in the lipoxygenase cascade, which have been shown to mediate several aspects of inflammatory and allergic response. The assay of this Example measures the ability of the compounds of the invention to inhibit the synthesis of 5-HETE by rat glycogen elicited polymorphonuclear leukocytes.

The assay is carried out as follows:

Peritoneal PMN are obtained from female Wistar rats (150–250 g) that received an i.p. injection of 6% glycogen (10 ml). After 24 hours, rats are killed by $CO_2$ asphyxiation and peritoneal cells are harvested by peritoneal lavage using $Ca^{++}$ and $Mg^{++}$ free Hanks' balanced salt solution (HBSS). The peritoneal exudate is centrifuged at 400 g for 10 minutes. After centrifugation, the lavaged fluid is removed and the cell pellet is repeated in HBSS containing $Ca^{++}$ and $Mg^{++}$ and 10 mM L-cystein at a concentration of $2 \times 10^7$ cells/ml. To 1 ml portions of cell suspens, test drugs or vehicle are added and incubated at 37° C. for 10 minutes. Following this preincubation, the calcium ionophore (10 μM), A23187, is added together with 0.5 μCi [$^{14}$C] arachidonic acid and further incubated for 10 minutes. The reaction is stopped by the addition of ice cold water (3 ml) and acidifying to pH 3.5. Lipoxygenase products are then extracted twice into diethyl ether. The pooled ether extracts are evaporated to dryness under nitrogen and the residue is redissolved in a small volume of methanol and spotted on aluminum backed pre-coated thin layer chromatographic plates. The samples are then co-chromatographed with authentic reference 5-HETE in the solvent system—hexane:ether:acetic acid (50:50:3). After chromatography, the areas associated with 5-HETE standard are identified by autoradiography, cut out and quantitated by liquid scintillation.

Results are expressed as % inhibition of [$^{14}$C]5-HETE synthesis.

$$\% \text{ inhibiton} = \frac{\text{control} - \text{test}}{\text{control}} \times 100$$

Testing compounds of the invention in this assay, the following results are obtained.

TABLE I

| Compound of Example Number | % Inhibition at 50 μm | 50% Inhibitory Concentration (IC$_{50}$)μm |
|---|---|---|
| 1 | + | 40.4 |
| 2A | + | 16.4 |
| 2B | + | 2.4 |
| 2C | − | |
| 2D | − | |
| 2E | + | |
| 2F | + | |
| 2G | + | |

+ = >50%;  − = <50%

The results show that compounds of this invention have significant activity in inhibiting the synthesis of the arachidonic acid lipoxygenase oxidation product 5-HETE.

EXAMPLE 11

The assay of this Example measures the in vivo ability of the compounds of the invention to inhibit the bronchospasm induced in guinea pigs by the exogenously administered leukotrienes C$_4$ and/or D$_4$. This assay is essentially a measure of the SRS-A antagonist properties of the compounds tested.

This assay is carried out as follows:

Male Hartley strain guinea pigs (350–600 g) are anesthetized with pentobarbital sodium (50 mg/kg, i.p.). The jugular vein is cannulated for injection of drugs and the carotid artery for monitoring blood pressure. The trachea is cannulated for artificial ventilation by a miniature Starling pump and for indirect measurement of respiratory volume changes as described infra. Additional pentobarbital sodium (15 mg/kg, i.v.) is administered to arrest spontaneous respiration. Submaximal bronchoconstrictor responses are established in control animals by varying the dose-levels of leukotriene. Intravenous dose-levels for LTC$_4$ range from 1 to 2 μg/kg and for LTD$_4$ the range is from 0.3 to 1 μg/kg. The aerosol bronchoprovocation dose for LTC$_4$ is generated from 1.6 μM solution and for LTD$_4$ from a 2.0 μM solution.

Test drugs are administered either intravenously, by aerosol or orally at 1 or 10 minutes before induction of bronchospasm by administration of either LTC$_4$ or LTD$_4$ at the predetermined dose-levels. Aerosols of soluble drugs or leukotrienes are produced in-line for 10 seconds only by actuation of an ultrasonic nebulizer (Monaghan). Aerosolized drug dosage is expressed in terms of solution concentration and by a fixed aerosol exposure time (approximately 10 seconds). Control animals receive saline in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at 1, 3 and 5 minutes are obtained from the recorded charts.

Area under the volume overflow curve (AUC) is estimated, using the overflow values at 1, 3 and 5 minutes, and expressed as a percentage of the maximum overflow AUC (equation 1):

$$\% \max AUC = \frac{3(1 \text{ min}) + 4(3 \text{ min}) + 2(5 \text{ min})}{10(\max)} \times 100 \quad (1)$$

Drug effects reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Student's t-test for unpaired data is used to determine statistical significance (p<0.05). IC$_{50}$ values can also be determined by inverse prediction from linear regression lines through points between 10 and 90% inhibition.

The results for compounds of the invention are as follows:

TABLE 2

| | Compound administered at 10 minutes before induction of bronchospasm | |
|---|---|---|
| Compound of Example Number | Dose mg/kg (Intraduodenal) | % Ihibition of Max AUC |
| 1 | 50 | 59.2 |
| 2A | 50 | 77.2 |
| 2B | 50 | 81.8 |
| 2C | 50 | 63.9 |
| 2D | 50 | 43.9 |
| 2E | 50 | 21.0 |
| 2F | 50 | 92.6 |
| 2G | 50 | 65.1 |
| 2H | 50 | 56.0 |
| | 50* | 25.4 |
| 2I | 50 | 71.2 |
| 2J | 50 | 83.4 |
| 2K | 50 | 70.6 |
| 2L | 25 | 35.6 |
| 3 | 50 | 81.7 |
| | 25 | 94.9 |
| 4 | 50 | 92.3 |
| | 25 | 79.0 |
| 4 | 25* | 18.4 |
| 5 | 50 | 54.2 |
| | 50* | 18.6 |
| 6 | 25 | 19.8 |
| 7A | 25 | 18.1 |
| 7B | 25 | 81.9 |
| 7C | 25 | 24.9 |
| 8 | 25 | 41.2 |
| 9 | 25 | 84.8 |
| | 25* | 75.6 |

*peroral administration

The results show that compounds of the invention have significant in vivo activity against LTD$_4$ induced bronchoconstriction.

EXAMPLE 12

The assay of this Example measures the in vivo ability of the compounds of the invention to inhibit the bronchospasm induced in guinea pigs by endogenous mediators of the bronchoconstriction.

The assay is carried out as follows:

Male Hartley strain guinea pigs weighing 250–350 g are sensitized to chicken ovalbumin (OA) (10 mg i.p.) on days 1 and 3 and used starting on day 26. The animals are anesthetized with pentobarbital sodium (50 mg/kg, i.p.), bilateral vagotomy is performed, and the jugular vein is cannulated for injection of drugs and the carotid artery for monitoring blood pressure. The trachea is cannulated for artificial ventilation by miniature Starling pump and for indirect measurement of respiratory volume changes as described, infra. Succinylcholine (2 mg/kg, i.v.) is administered to arrest spontaneous respiration. A cyclooxygenase inhibitor, indomethacin (10 mg/kg in tris buffer, i.v. at 9 min.) is administered to shunt arachidonic metabolism to lipoxygenase pathways. One minute later, chlorpheniramine (1.0 mg/kg in saline, i.v.) is given to attenuate the histaminic component of anaphylactic bronchoconstriction. Test drugs (dissolved in propylene glycol, polyethylene glycol or saline) are administered either intraduodenally or by aerosol at 2 or 10 minutes before antigen challenge. Anaphylactic bronchoconstriction is induced by administration by breaths of aerosolized OA (1%) or by intravenous administration of 0.1–0.3 mg/kg OA in saline. Control animals receive solvent (2 ml/kg i.d. or appropriate aerosol) in place of drug.

Respiratory volume changes are determined by a calibrated piston whose travel is recorded, via a linear transducer, on a Beckman Dynograph recorder. Maximal bronchoconstrictor volume is determined by clamping off the trachea at the end of the experiment. Overflow volumes at minutes 1, 3 and 5 are obtained from the recorded charts.

Area under the volume overflow curve (AUC) is estimated, using the overflow values at 1, 3 and 5 minutes, and expressed as a percentage of the maximal overflow AUC (equation 1):

$$\% \max AUC = \frac{3(1 \min) + 4(3 \min) + 2(5 \min)}{10(\max)} \times 100 \quad (1)$$

Drug effects are reported as percent inhibition of % max AUC values obtained from appropriate control animals (equation 2):

$$\% \text{ inhibition} = \frac{\% \max AUC \text{ control} - \% \max AUC \text{ treated}}{\% \max AUC \text{ control}} \times 100 \quad (2)$$

Students t-test for unpaired data is used to determine statistical significance. Dose response curves are generated and ED$_{50}$ doses are interpolated from the regression lines.

Results for compounds of the invention in this assay, using LTD$_4$ for induction of bronchospasm, are given below:

TABLE 3

Compound administered at 10 minutes before intraduodenally administered ovalbumin challenge

| Compound of Example Number | Dose mg/kg (Intraduodenal) | % Inhibition of Max AUC |
|---|---|---|
| 2A | 50 | 83.4 |
| 2B | 50 | 75.8 |
| 2C | 50 | 65.6 |
| 2H | 50 | 2.5 |
| 2I | 50 | 22.5 |
| 2J | 25 | 81.2 |
| 3 | 50* | 46.4 |
| 4 | 25 | 95.4 |
| 5 | 50 | 80.2 |

*peroral administration

The results show that compounds of the invention have significant in vivo activity in inhibiting ovalbumin induced bronchospasm mediated by endogeneous products of the lipoxygenase oxidation of arachidonic acid.

What is claimed is:

1. A compound having the formula:

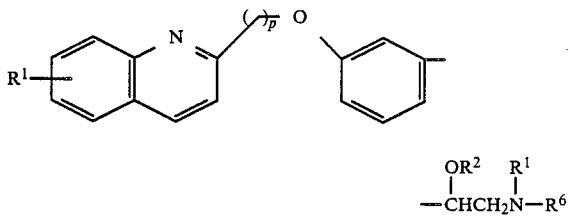

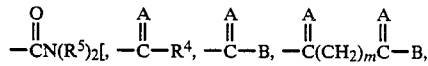

wherein
p is 0–3;
R$^1$ is hydrogen or lower alkyl;
R$^2$ is H or

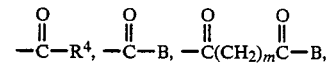

R$^3$ is H, lower alkyl or perfluoro lower alkyl;
R$^4$ is phenyl, pyridyl or thienyl;
R$^5$ is hydrogen, lower alkyl, phenyl or pyridyl;
R$^6$ is $$-\overset{O}{\underset{\|}{C}}-R^4, \quad -\overset{O}{\underset{\|}{C}}-B, \quad -\overset{O}{\underset{\|}{C}}(CH_2)_m\overset{O}{\underset{\|}{C}}-B,$$

—SO$_2$R$^3$, —SO$_2$N(R$^3$)$_2$, lower alkynyl or lower alkyl carbonyl prolinate;
B is OR$^1$ or N(R$^5$)$_2$;
m is 0–2;
and the pharmaceutically acceptable salts thereof.

2. The compound of claim 1, which is (1R)-1-[3-[(2-quinolinyl)methoxy]phenyl]-2-(N-methyl-N-diethylcarbamoyl)amino ethanol.

3. The compound of claim 1, which is (1R)-1-[3-[(2-quinolinyl)methoxy]phenyl]-2-[N-methyl-N-(4-pyridonyl)]amino ethanol.

4. The compound of claim 1, which is (1R)-1-[3-[(2-quinolinyl)methoxy]phenyl]-2-(N-methyl-N-diphenylcarbamoyl)amino ethanol.

5. The compound of claim 1, which is (1R)-1-[3-[(2-quinolinyl)methoxy]phenyl]-2-(N-methyl-N-dimethylcarbamoyl)amino ethanol.

6. The compound of claim 1, which is (1R)-1-[3-[(2-quinolinyl)methoxy]phenyl]-2-(N-ethyl-N-diethylcarbamoyl)amino ethanol.

7. The compound of claim 1, which is (1R)-1-[3-[(2-quinolinyl)methoxy]phenyl]-2-(N-methyl-N-dimethylsulfamoyl)amino ethanol.

8. The compound of claim 1, which is (S)-1-[[[(R)-2-hydroxy-2-[3-(2-quinolinylmethoxy)phenyl]ethyl]methylamino]carbonyl]-2-pyrrolidine carboxylic acid, methyl ester.

9. The compound of claim 1, which is (1S)-1-[3-[(2-quinolinyl)methoxy]phenyl]-2-(N-methyl-N-diethylcarbamoyl)amino ethanol.

10. The compound of claim 1, which is (1R)-1-[3-[(2-quinolinyl)methoxy]phenyl]-2-(N-methyl-N-ethylcarboxylate)amino ethanol.

11. The compound of claim 1, which is 1-[3-[(2-quinolinyl)methoxy]phenyl]-2-(N-ethylcarboxylate)amino ethanol.

12. The compound of claim 1, which is (1R)-1-[3-[(2-quinolinyl)methoxy]phenyl]-2-(N-ethylcarbamoyl)amino ethanol.

13. The compound of claim 1, which is (1R)-1-[3-[(2-quinolinyl)methoxy]phenyl]-2-(N-methylcarbamoyl)amino ethanol.

14. The compound of claim 1, which is ethylcarbamic acid (1R)-2-[[(ethylamino)carbonyl]methylamino]-1-[3-(2-quinolinylmethoxy)phenyl]ethyl ester.

15. The compound of claim 1, which is N-[2-hydroxy-2-[3-(2-quinolinylmethoxy)phenyl]ethyl]-2-pyridine carboxamide.

16. The compound of claim 1, which is N-[2-hydroxy-2-[3-(2-quinolinyl)phenyl]ethyl]benzamide.

17. The compound of claim 1, which is N-[2-hydroxy-2-[3-(2-quinolinylmethoxy)phenyl]ethyl]-2-thiophene carboxamide.

18. The compound of claim 1, which is 3-[[2-hydroxy-2-[3-(2-quinolinylmethoxy)phenyl]ethyl]amino]-3-oxapropanoic acid, ethyl ester.

19. The compound of claim 1, which is α-[[methyl-(2-propynyl)amino]methyl]-3-(2-quinolinylmethoxy)benzene methanol.

20. The compound of claim 1, which is 1,1,1-trifluoro-N-[2-hydroxy-2-[3-(2-quinolinylmethoxy)phenyl]ethyl]methane sulfonamide.

* * * * *